United States Patent
Cefai

(10) Patent No.: US 10,854,325 B2
(45) Date of Patent: Dec. 1, 2020

(54) COMMUNICATION HANDLING

(71) Applicant: ViCentra B.V., Utrecht (NL)

(72) Inventor: Joseph Cefai, Swansea (GB)

(73) Assignee: Vicentra B.V., Utrecht (NL)

( * ) Notice: Subject to any disclaimer, the term of this patent is extended or adjusted under 35 U.S.C. 154(b) by 112 days.

(21) Appl. No.: 16/092,618

(22) PCT Filed: Apr. 20, 2017

(86) PCT No.: PCT/EP2017/059336
§ 371 (c)(1),
(2) Date: Oct. 10, 2018

(87) PCT Pub. No.: WO2017/190959
PCT Pub. Date: Nov. 9, 2017

(65) Prior Publication Data
US 2019/0172574 A1    Jun. 6, 2019

(30) Foreign Application Priority Data
May 6, 2016    (GB) .................... 1607981.6

(51) Int. Cl.
*G16H 20/17* (2018.01)
*G06F 19/00* (2018.01)
(Continued)

(52) U.S. Cl.
CPC ............ *G16H 20/17* (2018.01); *A61M 5/172* (2013.01); *G06F 19/3418* (2013.01);
(Continued)

(58) Field of Classification Search
None
See application file for complete search history.

(56) References Cited

U.S. PATENT DOCUMENTS

| 4,395,259 A | 7/1983 | Prestele et al. |
| 2013/0317753 A1* | 11/2013 | Kamen .................. G16H 40/20 702/19 |
| 2015/0207626 A1* | 7/2015 | Neftel .................... G08C 17/02 713/168 |

FOREIGN PATENT DOCUMENTS

| GB | 2175724 A | 12/1986 |
| JP | S6195636 A | 5/1986 |

(Continued)

OTHER PUBLICATIONS

International Search Report and Written Opinion for International Application No. PCT/EP2017/059336, dated Jul. 10, 2017, 9 pages.

(Continued)

*Primary Examiner* — Mohammad Ali
*Assistant Examiner* — Saad M Kabir
(74) *Attorney, Agent, or Firm* — Armstrong Teasdale LLP

(57) ABSTRACT

A system and method for processing instructions sent wirelessly between a control master unit and a slave device comprising a slave device memory is disclosed. The control master unit transmits an instruction to the slave device. The slave device writes the received instruction to the slave device memory; reads a stored instruction, corresponding to the instruction written to the memory, from the memory; and transmits the stored instruction to the control master unit. The control master unit compares the stored instruction to the instruction and, if the stored instruction is the same as the instruction, enables a process instruction to be sent to the slave device. In response to receiving the process instruction, the slave device processes the stored instruction.

21 Claims, 6 Drawing Sheets

(51) Int. Cl.
  *H04W 4/90* (2018.01)
  *A61M 5/172* (2006.01)
  *H04B 5/00* (2006.01)
  *H04W 84/20* (2009.01)

(52) U.S. Cl.
  CPC ....... *G06F 19/3468* (2013.01); *H04B 5/0031* (2013.01); *H04W 4/90* (2018.02); *A61M 2202/07* (2013.01); *A61M 2205/3569* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2230/201* (2013.01); *H04W 84/20* (2013.01)

(56) References Cited

FOREIGN PATENT DOCUMENTS

| JP | S62219730 A | 9/1987 |
|---|---|---|
| JP | H0195636 A | 4/1989 |
| WO | 2014009876 A2 | 1/2014 |

OTHER PUBLICATIONS

Near field communication. Wikipedia, the free encyclopedia, Feb. 7, 2015, retrieved on May 25, 2016.

\* cited by examiner

COMMUNICATION HANDLING

CROSS-REFERENCE TO RELATED APPLICATIONS

This application is the 35 U.S.C. § 371 national stage of PCT/EP2017/059336, filed Apr. 20, 2017, which claims priority to British Patent Application No. 1607981.6, filed May 6, 2016, which are incorporated herein by reference in their entirety.

TECHNICAL FIELD

The present invention relates to wireless data communications between a control master unit and a slave device, in particular a slave device for delivering therapy to a patient.

BACKGROUND

Infusion systems for the infusion of liquid therapeutic products into the human or animal body are known in the art, e.g. from U.S. Pat. No. 4,395,259. Such systems are particularly, though not exclusively, intended for the infusion of insulin into the body for diabetes therapy. The system has an infusion slave device which may be implanted or worn externally on the body, and a remote controller that can wirelessly monitor the function of the infusion slave device.

The controller can be used to send instructions wirelessly to the pump. The instructions, when processed, cause the pump to deliver fluid through the infusion slave device. It is critical the slave device delivers fluid exactly as instructed to by the controller.

SUMMARY OF INVENTION

At its most general, the present invention provides a system and method for preventing corrupt and incorrect commands from being processed by a slave unit wirelessly controlled by a remote control master unit. The slave unit receives a command instruction from the control master unit, writes the command instruction to a memory to create a stored instruction, reads the stored instruction from the memory, and transmits the read stored instruction to the control master unit. The control master unit compares the received stored instruction with the command instruction and, only if the stored instruction does not differ from the command instruction, sends a process instruction to the slave unit.

According to a first aspect of the present invention, there is provided a system and a method, wherein the system is configured to perform the method. The system comprises a slave device and a control master unit for controlling the slave device. The slave device comprises a slave device memory and a slave device processor, and the control master unit comprises a control master unit memory and a control master unit processor. The slave device and the control master unit are capable of communicating wirelessly with each other. The method comprises transmitting, from the control master unit to the slave device, a wireless command signal containing a command instruction; and at the slave device: writing the command instruction to the slave device memory to create a stored instruction; reading the stored instruction from the slave device memory; and transmitting, to the control master unit, a wireless response signal containing the stored instruction. The invention further comprises comparing, at the control master unit, the stored instruction to the command instruction. If the stored instruction is the same as the command instruction, a process instruction is sent to the slave device.

The invention thus prevents corrupted or otherwise incorrect instructions from being processed by the slave device. By ensuring that only if the stored instruction held by the slave device is the same as the command instruction originally sent by the control master unit will the slave unit be able to process that stored instruction, even if an instruction is corrupted when stored in the slave device memory or during transmission it will not be processed.

Known systems and methods require complicated exchanges of messages and "handshaking" between the control master unit and the slave device for determining whether the instruction has been received, stored and processed. Such exchanges require the slave device to retain, process and transmit significant amounts of data, and as such the slave device requires significant processing capability, memory and associated battery power. In contrast, the device and method of the present invention is very simple. A slave device according to the invention requires very little programming, memory or processing capability. The device is not complex, it can be simply manufactured and requires minimal components and programming. The device can thus be relatively small, which is particularly advantageous in embodiments in which the slave device comprises a wearable device.

The term slave device is used herein to refer to a device whose operation is controlled by a remote control master unit. That is, a slave device is a device which carries out an operation in response to processing of a command instruction sent by a control device. The slave device will typically incorporate a drive member, actuating part or similar for carrying out that operation.

The term command instruction refers to an instruction, or directive, issued by the control master unit to direct the operation of the slave unit. Similarly, process instruction refers to an instruction, or directive, issued by the control master unit to direct the slave unit to process a received instruction, preferably the command instruction or stored instruction. The stored instruction refers to the copy of the command instruction saved in the memory of the slave unit.

The slave device preferably includes an effector, and the command instruction is for operating the effector. Preferably the command instruction is exclusively for operating the effector. Preferably the slave device memory is exclusively for storing the command instruction. In an embodiment, the effector is an actuator for a fluid pump. Preferably the slave device is devoid of any user interface for operating the effector such that the only way to operate the effector is via the command instruction communicated wirelessly by the control master unit.

The system may be a medical system and the slave device is preferably a delivery device for delivering therapy to a patient. Processing the stored instruction comprises delivering therapy to a patient. Medical systems often employ wireless slave devices, particularly slave devices to be worn by a patient. In the medical field, it is essential that the correct therapy is delivered to a patient. An incorrect dose of therapy could be dangerous.

The medical system may be a fluid delivery system, and the delivery device may be a pumping device for pumping a therapeutic fluid wherein processing the stored instruction results in pumping the fluid into e.g. the subcutaneous tissue of a user. Fluid delivery is a field where wireless control of a delivery slave device, often a wearable delivery slave device, is desirable. Further, fluid delivered directly to a patient must be delivered in precise and correct dose. A delivery of too much or too little fluid could be dangerous.

The therapeutic fluid may be insulin. Insulin is delivered for the treatment of diabetes through a wearable insulin infusion system. Precise control over the volume and timing of fluid delivery is needed to control blood sugar levels in a diabetic. Any departure from the desired fluid delivery instructions could be dangerous to the user.

The slave device may be configured to store only a single instruction in the memory at any one time. If the slave device memory can only store one instruction at a time, there is no chance of the memory mixing up different instructions, or reading a different instruction from the different part of the memory. Therefore the slave device will be more reliable to process the correct instruction. Further, a memory which can only store one instruction at a time does not require a large processor or storage space, leading to a smaller slave device. A slave device may be a wearable device, and in such embodiments it is particularly desirable to reduce the size and weight of the slave device.

The method may further include, at the slave device, receiving the process instruction from the control master unit, and processing the stored instruction only once a process instruction has been received. This ensures that an instruction stored in the device memory is not processed until the device receives confirmation that the instruction has not been corrupted on storing, and therefore provides a safe system.

The step of writing the command instruction to the slave device memory may comprise writing the instruction to a location in the slave device memory; and the step of reading the stored instruction from the memory may comprise reading the stored instruction from the location in the slave device memory. Ensuring that the instruction sent to the control master unit is read from the same location of the memory as the instruction is stored ensured that the control master unit received an accurate representation of the instruction corresponding to the present instruction which is stored in the slave device memory. If the stored instruction sent to the control master unit was read from a different location, the instruction processed by the slave device may be different to that verified by the control master unit, leading to an inaccurate instruction being processed.

The method step of writing the command instruction to the memory may have a finite probability of being subject to corruption. The method provides a verification that the command instruction has not been corrupted, before allowing the slave device to process the command instruction. To do this the system compares the instruction stored in the slave device memory to the command instruction before issuing a process instruction.

The slave device and the control master unit may be able to communicate wirelessly using a radio frequency near field communication protocol. This allows the control master unit and slave device to communicate when within a given range of one another. Radio frequency near field communication protocol requires only a low amount of power, therefore the battery in the slave device can be small and compact. A small slave device is desirable, especially in situations where the slave device forms a wearable device.

The invention may also comprise, at the control master unit, if the stored instruction is the same as the command instruction: requiring a user input; and, in response to receiving an affirmative user input, sending a process instruction to the slave device. The user is provided with the opportunity to confirm that they wish to proceed with the command.

Alternatively, the invention may also comprise, at the control master unit, if the stored instruction is the same as the command instruction: automatically sending a process instruction to the slave device. Once it has been determined the command instruction has been correctly stored, no further user input is required and the slave device automatically processes the command instruction. This speeds up processing of the instruction and relieves the user of undue burden.

BRIEF DESCRIPTION OF THE DRAWINGS

For a better understanding of the present invention, and to show more clearly how it may be carried into effect, reference will now be made, by way of example, to the following drawings, in which.

DETAILED DESCRIPTION

Figure 1:
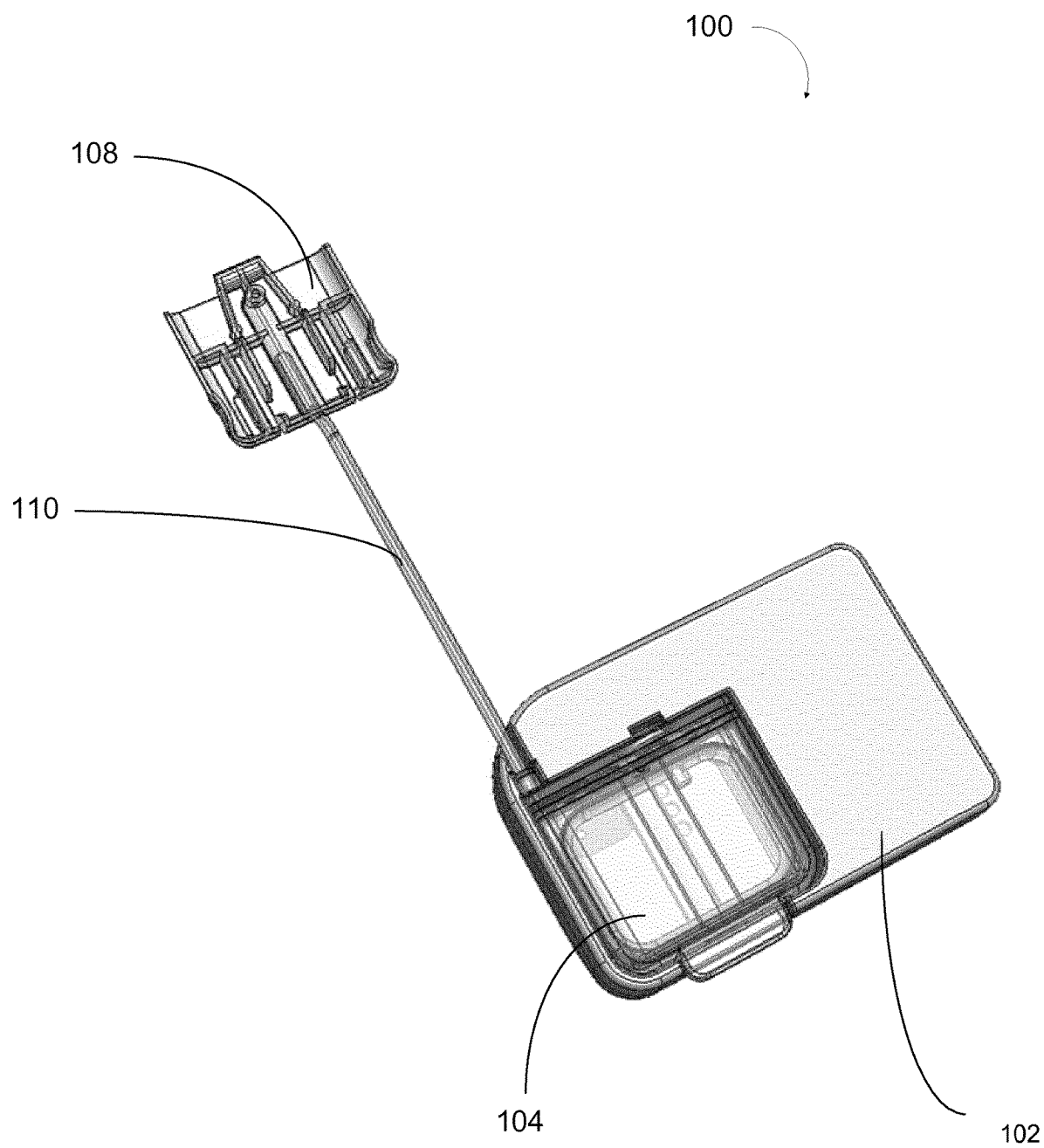
FIG. 1 shows a slave device for infusion of fluid into the human body.

FIG. 1 shows the wearable part of an external infusion system for the continuous subcutaneous infusion of insulin into the human body through repetitive small pulses of infusion. The infusion slave device 100 comprises a pump part 102, a replaceable cartridge 104 having an outlet port 106 connected to an infusion set 108 via an infusion tube 110.

Depending on the desired positioning of the pump part 102 with respect to the infusion set 108 during use, the length of the infusion tube 110 may be longer or shorter than that shown in FIG. 1, and indeed the infusion set 108 may be coupled directly to the output port 106 of the pump where close coupling of the infusion set 108 and the pump part 102 is desired, thereby avoiding the need for the flexible infusion tube 110.

The cartridge 104 includes a reservoir for storing a supply of insulin and a pumping chamber. The cartridge may be disposable and removably attached to a durable housing part of the infusion system. When the cartridge 104 is attached to the housing a drive member of the pump part 102 is operatively coupled to the pumping chamber for delivering a supply of insulin from the reservoir to the outlet port 106 and into the infusion set 108 via the infusion tube 110.

The infusion set includes a subcutaneous cannula and an adhesive mount for adhering the infusion set to the patient's skin. The cannula is typically made of flexible plastic so as not to cause discomfort for the patient during use. The infusion set is typically installed into a spring loaded insertion slave device together with a steel needle surrounding the cannula. Upon insertion, the steel needle is removed leaving the cannula in place. Alternative infusion sets, which may replace the infusion set shown in FIG. 1, comprise a steel needle instead of the cannula. Thus insulin is infused through the cannula into the human body.

It will be appreciated that any other kind of slave device in wireless communication with a control master unit can be used in accordance with the present invention, the delivery system of FIG. 1 is just one example.

For example, the present invention could also be applied to blood glucose monitors, body worn biometric sensors including but limited to continuous glucose monitors, implantable medical devices such as pacemakers, digestible devices like so-called 'smart' pills, and activity monitors. In each case, there would be a benefit of the command/communication to perform a task being as small and as simple as possible. For example a smart pill may utilise wireless communication to initiate an action and the 'go' signal could be confirmed using the present invention.

Figure 2:
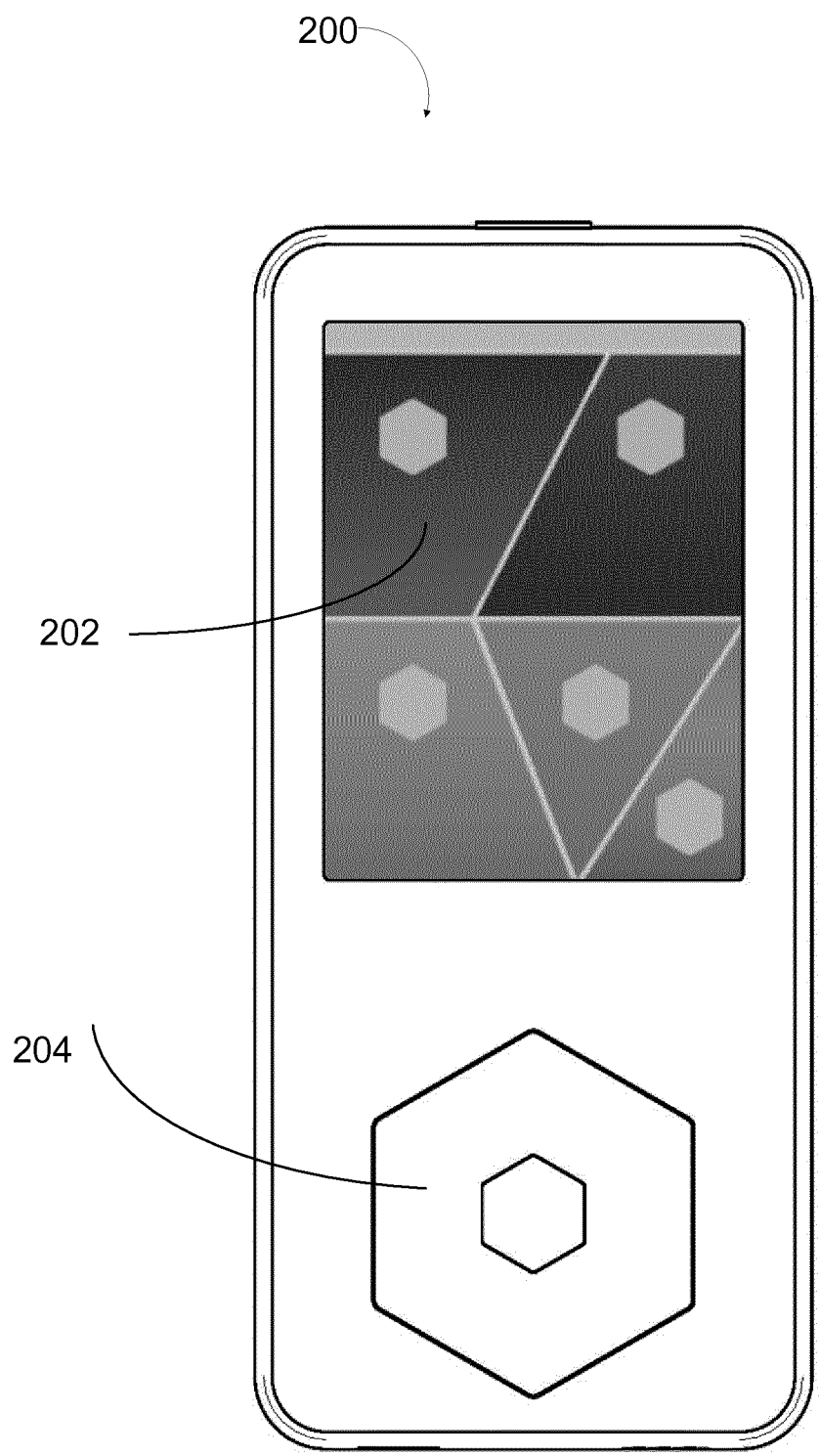
FIG. 2 shows a control master unit for controlling the slave device of FIG. 1.

FIG. 2 shows a control master unit 200 for wirelessly controlling the slave device 100. The control master unit 200 includes a graphical user interface 202 and a tactile user interface 204.

The control master unit 200 can be used to instruct the slave device to pump insulin from the cartridge through the infusion system. The control master unit may instruct the volume of fluid to be delivered, the rate of delivery, the duration of delivery, start time, stop times, or any similar instruction to control the fluid delivery from the slave device.

The control master unit 200 further enables a user to perform the following functions:

Define and store basal profiles;
Transfer an active basal profile to the slave device 100;
Define and transmit a bolus request to the slave device 100;
Define and transmit a temporary basal to the slave device 100;
View a graphical representation of a bolus based on glucose readings from a separate blood glucose meter or entered manually following a blood glucose meter reading from a separate blood glucose meter (not shown);
View graphically pump performance over time;
Request the current status of the slave device 100 (including what insulin delivery is currently in progress, battery status, alarm conditions, insulin reservoir level, etc).

The reader will appreciate that the slave device must accurately perform the instructions which are sent by the control master unit. If the instruction processed by the slave device differs in any way from the instruction sent by the control master unit, the slave device may deliver an incorrect volume of fluid. In the field of insulin delivery, this may be dangerous.

Embodiments of the present invention provide a system and method for ensuring correct processing by a slave device of an instruction sent from a control master unit.

Figure 3:
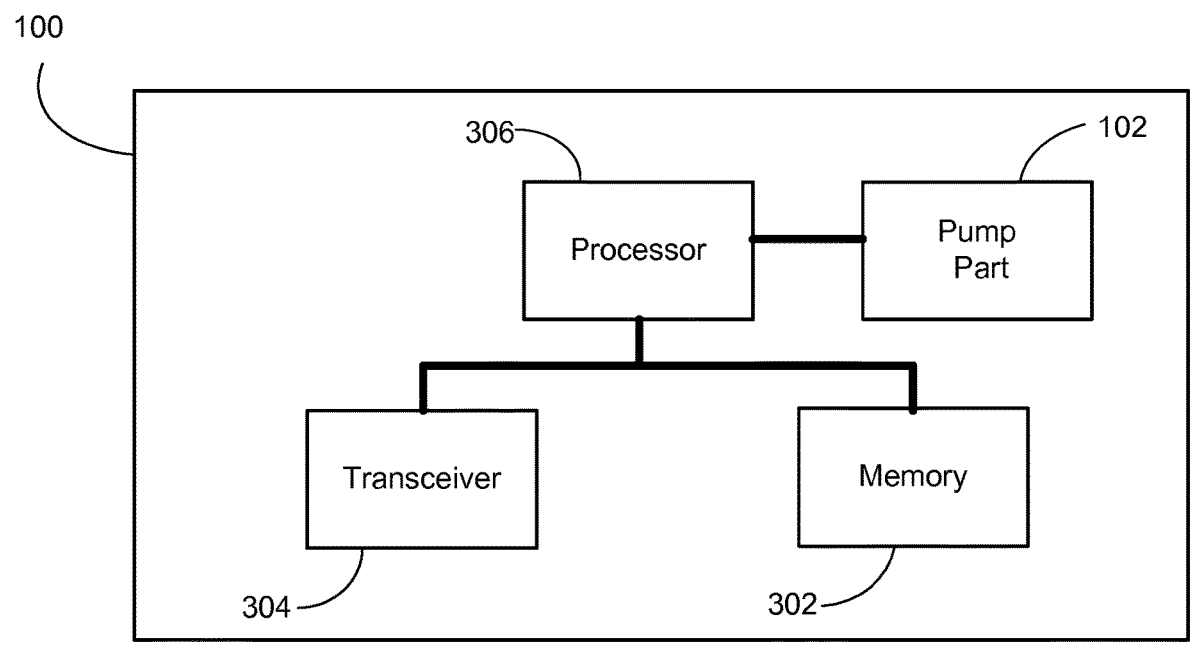
FIG. 3 shows a schematic representation of a slave device according to the present invention.

FIG. 3 shows a schematic representation of the slave device 100. For clarity, some features of the slave device 100, such as the replaceable cartridge 104 and infusion set 108, are not shown in FIG. 3. The slave device 100 includes a transceiver 304 for wireless communication with the control master unit 200. The wireless communication may be via BLUETOOTH™ or other radio frequency near field communication means.

The slave device further includes a slave device memory 302, which the slave device can write instructions to, and read instructions from. The slave device can receive an instruction from the control master unit 200 via the transceiver 304 and store the instruction in the slave device memory 302. It will be appreciated that a separate transmitter and receiver could be used in place of the transceiver 304.

The slave device 100 further includes a slave device processor 306 for processing instructions. The slave device 100 can read an instruction from the slave device memory 302 and process it using the processor 306.

The slave device 100 also includes the pump part 102, which may in some embodiments be replaced by another actuating part. The slave device can operate the pump in response to command instructions processed by the processor 036.

The features shown in FIG. 3 are those relevant to the present invention, and the skilled person will understand that the slave device may include further elements, such as a power source for powering the slave device.

Figure 4:
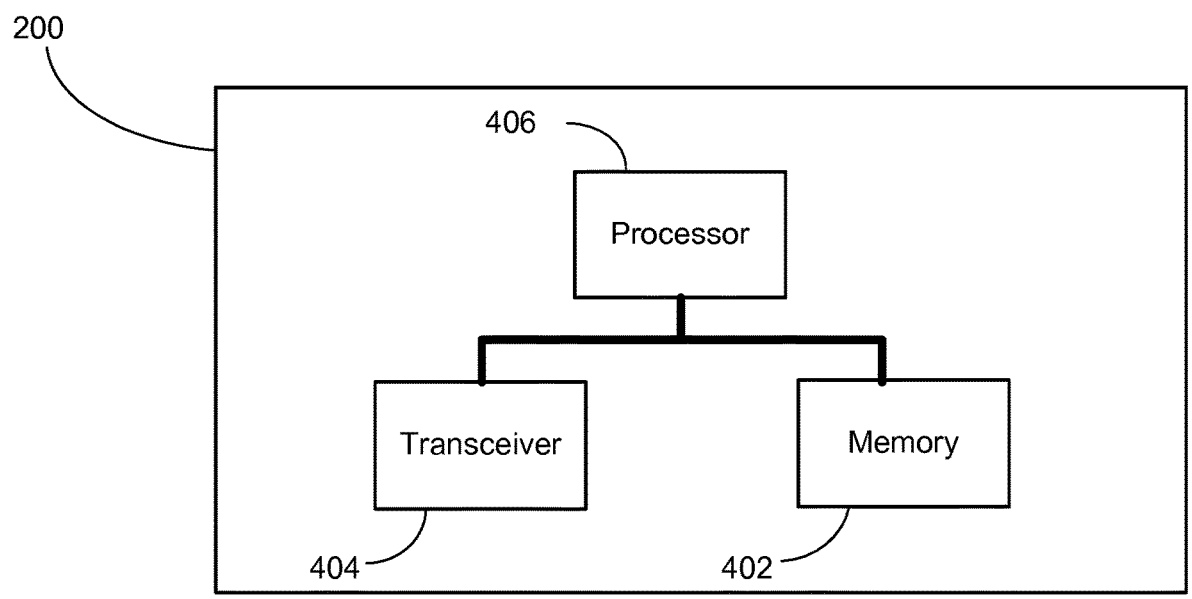
FIG. 4 shows a schematic representation of a control master unit according to the present invention.

FIG. 4 shows a schematic representation of the control master unit 200. The control master unit 200 includes a transceiver 404 for wireless communication with the slave device 100. The wireless communication may be via BLUETOOTH™ or other radio frequency near field communication means. The control master unit 200 is also BLUETOOTH™ or Wi-Fi enabled for internet connectivity. The internet connectivity enables two-way patient support either directly or via an intermediate internet connected slave device such as a PC, laptop or mobile slave device.

The control master unit includes a control master unit memory 402, which the control master unit can write instructions to, and read instructions from. The control master unit further includes a control master unit processor 306 for processing instructions.

The control master unit 200 can read instructions stored in the control master unit memory 402, and process them using the control master unit processor 406. Processing the stored instructions can cause the control master unit 200 to transmit wirelessly using the transceiver 404.

Therefore there is provided a system with a control master unit and a slave device which can communicate wirelessly with each other. The control master unit 200 transmits command instructions to the slave unit 100 which the slave unit 100 ultimately processes via the slave device processor 306. Presuming that no errors, corruptions, or other faults occur, the instruction processed by the slave device will correspond exactly to the instruction sent by the control master unit and the system functions correctly. However, there may be a corruption in writing the instruction to the memory, or in reading the instruction from the memory. If this happens then the instruction processed by the slave device might not correspond exactly to the instruction transmitted by the control master unit 200. The slave device will process an incorrect instruction, which leads to malfunctioning of the system. Embodiments of the present invention avoid such malfunctioning of the system.

Figure 5:
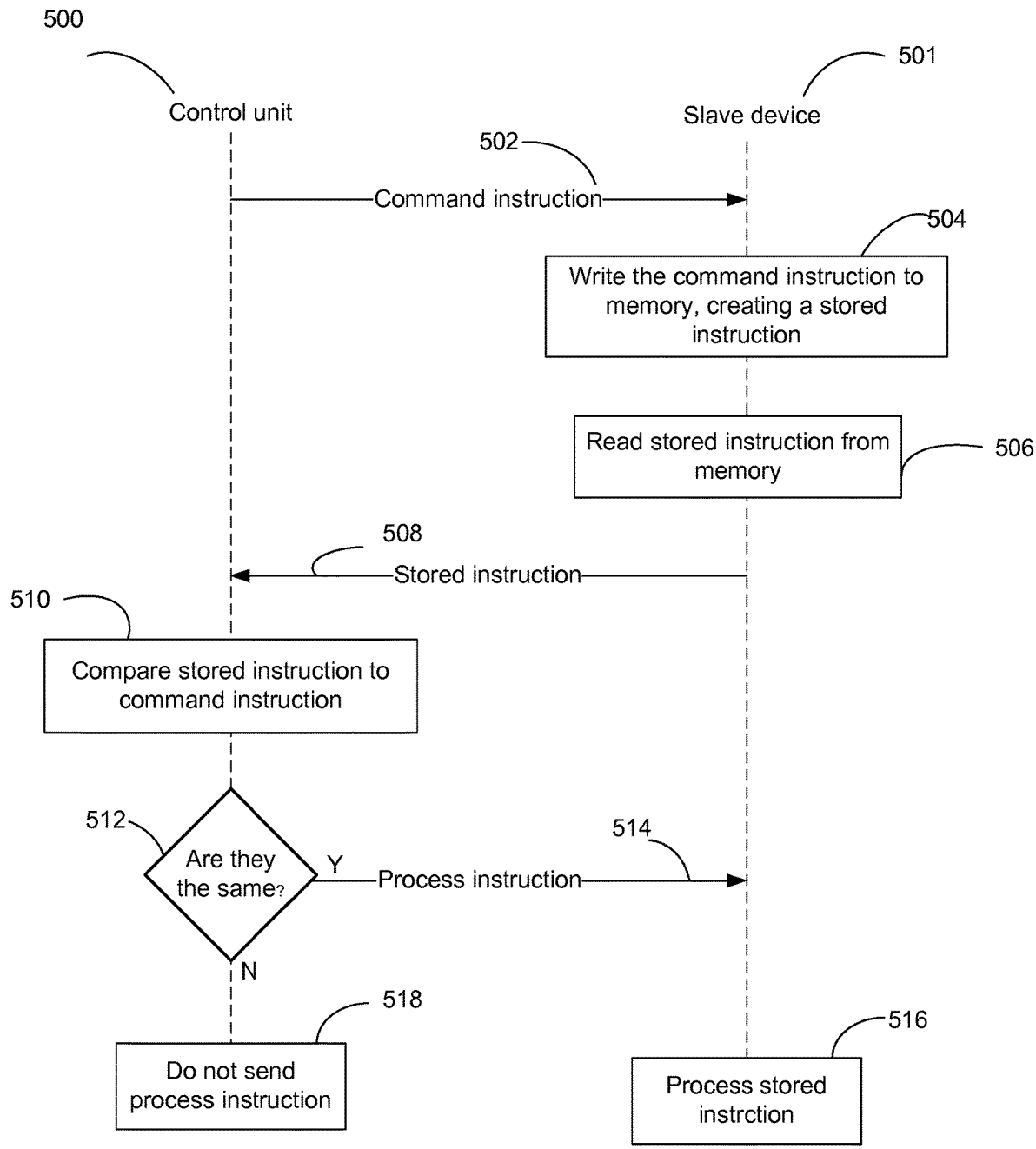
FIG. 5 shows a flow diagram illustrating a method of operating the slave device and control master unit of the present invention.

FIG. 5 shows a flow diagram of a process according to the present invention for wirelessly controlling a slave device 100 from a control master unit 200. The flow diagram includes a command line 500 for the control master unit, and a command line 501 for the slave device.

Arrows going between the two command lines indicate a communication, in the form of a wireless signal, between the control master unit 200 and the slave device 100. The directions of the arrow heads indicate the direction of the communication.

The process begins at step 502, where the control master unit 200 wirelessly transmits a command signal using the control transceiver 404. The wireless command signal will be received by the slave device 100 at the slave device transceiver 304. The wireless command signal includes a command instruction. The command instruction may be read from a series of instructions stored in the control master unit memory, or may be input by a user into the control slave device.

After the slave device 100 has received the wireless command signal, at step 504 the slave device stores the command instruction contained in the wireless command signal to the slave device memory 104 to create a stored instruction which corresponds to the command instruction.

The command instruction may be stored (as the stored instruction) in a specific location within the slave device memory. In preferred embodiments, the slave device memory is only able to store a single command instruction received from the control master unit at one time. There may be a single location (the "designated location") within the slave device memory for storing instructions received from the control master unit. When a first instruction is received, it is written into the designated location in the slave device memory. If a second instruction is then received by the slave device from the control master unit, this is written to the designated location. As the first instruction is already stored in the designated location, and the designated location can only store a single instruction, the second instruction overwrites the first instruction in the designated location. In other embodiments, the slave device memory 302 may be able to store multiple command instructions at any time.

The slave device 100 then, at step 506, reads the stored instruction from the slave device memory, the stored instruction corresponding to the instruction stored in step 504. For example, the stored instruction will be read from the same location in the memory as the instruction was stored in at step 504.

At step 508 the slave device sends a wireless response signal containing the stored instruction to the control master unit. The wireless response signal is sent using the slave device transceiver 304 and is received by the control master unit at the control master unit transceiver 404.

At step 510, the control master unit compares the stored instruction contained in the wireless response signal to the command instruction which was sent to the slave device in step 502.

If the control master unit finds that the stored instructions received from the slave device are the same as the instruction sent to the slave device, then the stored instruction has not been corrupted and it can be processed. The control master unit will thus send a process instruction to the slave device at step 514. The process instruction may be sent automatically once the determination in step 510 has been made. Alternatively, further user input may be required before the process instruction is sent, which is described in more detail below.

Upon receiving the process instruction, the slave device, at step 516, processes the stored instruction, which corresponds to the command instruction sent by the control master unit in step 502. The slave device will read the stored instruction from the slave device memory and process it using the processor. Processing the stored instruction may involve, in the fluid infusion example shown in FIG. 1, delivering a defined amount of fluid (e.g. insulin) to a patient's subcutaneous tissue. More specifically, it may involve powering an actuator or drive member to cause fluid to pump from the delivery slave device.

Once the stored instruction is processed in step 516, the instruction which was originally sent by the control master unit at step 502 has been executed. After the process instruction is sent from the control master unit, the control master unit may display a completion message on the user interface 202, confirming that the instruction has been processed.

There may, however, be a corruption in one or more of the steps preceding step 510. For example there could be a corruption when the instruction is written to the slave device memory in step 504, or when the stored instruction is read from the slave device memory in step 506. Such a corruption may cause the stored instruction sent from the slave device at step 508 to differ from the instruction sent to the slave device at step 502.

In this case, the stored instruction should not be processed by the slave device. Therefore, when the control master unit determines that the two instructions are not the same (i.e. not identical) in step 512, it proceeds to step 518 and does not send a process instruction. The slave device therefore will not receive a process instruction, and so is prevented from processing the stored instruction. This arrangement prevents a corrupt instruction from being processed by the slave device, because the slave device is unable to process the stored instruction without a process instruction instructing it to do so.

The control master unit may display an error message on the user interface 202. The error message may inform the user that the instruction has not been carried out. This will allow the user to re-enter the instruction again if necessary, or to enter a new instruction.

Figure 6:
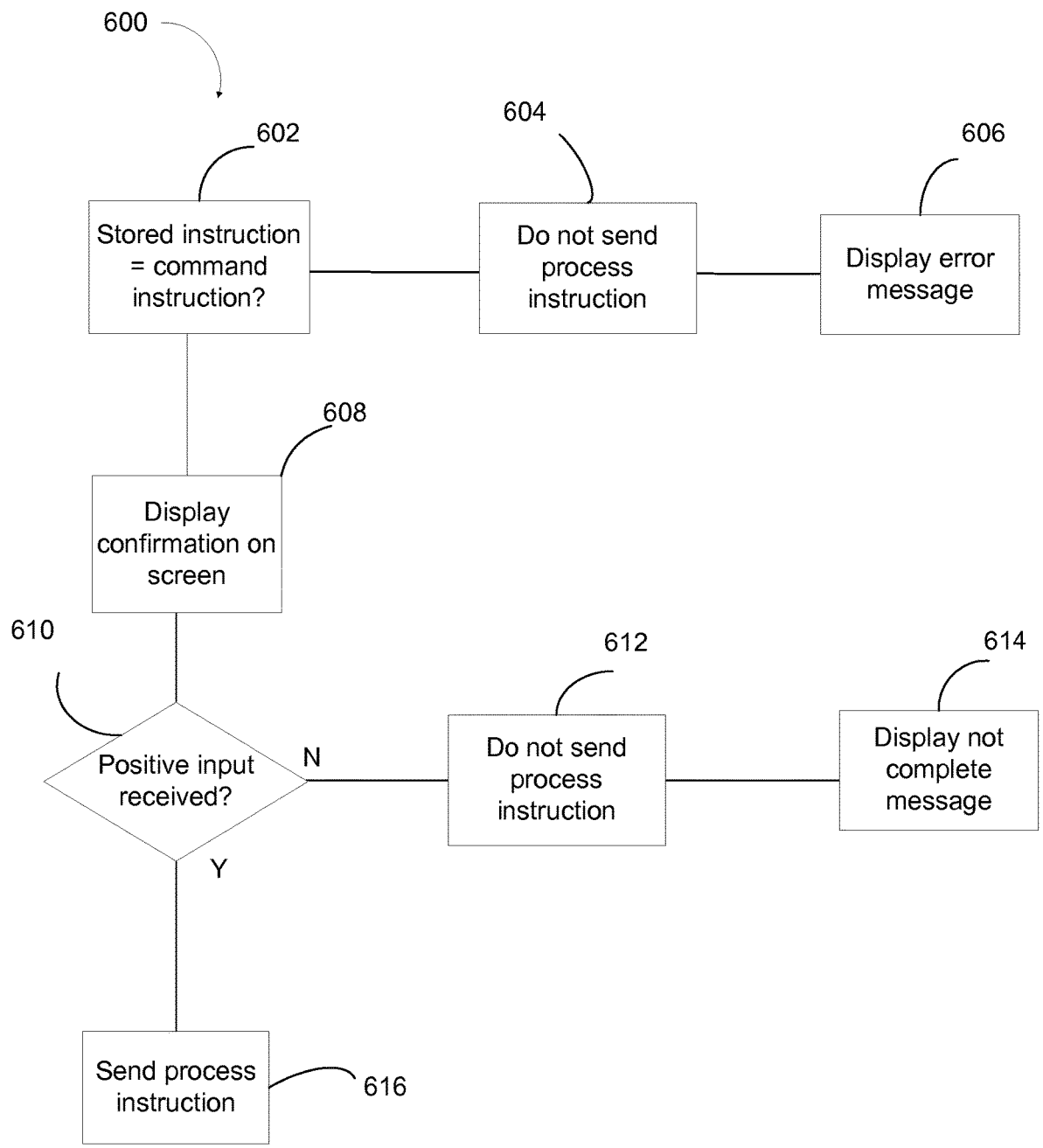
FIG. 6 shows a flow diagram of a process within the control master unit according to one aspect of the present invention.

FIG. 6 shows a flow diagram illustrating an embodiment in which the control master unit requires a positive user input before sending the process message to the slave device.

At step 602, the control master unit determines whether or not the stored instruction is the same as the command instruction. This corresponds to step 512 of FIG. 5.

If the two instructions are not the same then the control master unit is prevented from sending a process instruction at step 604 (corresponding to step 518 of FIG. 5), and the control master unit then, at step 606, displays an error message on the user interface 202. The error message informs the user that the command instruction has not been carried out. This will allow the user to re-enter the command instruction again if necessary, or to enter a new, different, instruction.

If the control master unit finds that, at step 602, the two instructions are the same, the control master unit proceeds to step 608 and displays a confirmation message on the user interface 202. The confirmation message may include a value read from the stored instruction or the command instruction.

For example, if the command instruction (or stored instruction) states "deliver 10 microliters", the confirmation message may display "Confirm deliver 10 microliters?" with a YES and a NO option. Alternatively, the control message may simply be "confirm command?" without reference to values read from either the command instruction or the stored instruction.

The control slave device then waits for a positive user input to be received at step 610. The user input may be in the form of a touch on the user interface, a keyboard entry, or selection using the tactile user interface 204. If the user is given a YES/NO option described above, selection of the input YES will classify as a positive user input.

If no positive user input is received, then the process instruction is not sent to the slave device, and the stored instruction is not processed (step 612). This could happen if a negative user input is received, for example if the user selects the NO option from the confirmation message described above. There will also be no positive input if no user input is detected within a certain time period, for example.

If no positive user input it received then the control master unit will, at step 614, display a message on the user interface 202, stating that the command instruction has not been processed. This will allow the user to re-enter the command instruction again if necessary, or to enter a new, different instruction.

If a positive user input is detected, then the control master unit will send a process instruction to the slave device at step 616 (corresponding to step 514 of FIG. 5). The slave device, upon receiving the process instruction, will process the stored instruction (step 516 of FIG. 5). Once the process instruction is sent from the control master unit, the control master unit may display a completion message on the user interface 202, confirming that the command instruction has been processed.

Following step 516 (or 616) the system may continue the process flow in any number of ways depending upon the specific system application and requirements. Examples may include:
- the slave device could be configured to erase the stored value after a given time period of inactivity
- the slave device may be configured to store a log of its action following the final process instruction
- the control unit could be configured to automatically repeat the process if step 518 (or 604 or 612) is reached (a counter could be included on the control unit to repeat the flow from step 502 a set number of times before reporting a communication failure to the user)
- the slave device may be configured to return additional information back to the control unit following the successful completion of 516 (or 616) and/or after a set or given time interval (this could be used as means for the slave device to provide evidence that it has continued to function long enough to complete the request command).

Embodiments of the present invention provide a method for processing instructions sent wirelessly between a control master unit and a slave device. Those skilled in the art will appreciate that various amendments and alterations can be made to the embodiments described above without departing from the scope of the invention as defined in the claims appended hereto.

The invention claimed is:

1. A system comprising:
a slave device comprising a readable and writeable slave device memory, a slave device processor, and a slave device transmitter-receiver; and
a control master unit for controlling the slave device, the control master unit comprising a control master unit readable and writeable memory, a control master unit processor, and a control master unit transmitter-receiver, wherein:
the slave device and the control master unit are capable of communicating wirelessly with each other via their respective transmitter-receivers;
the control master unit processor is configured to:
transmit via the control master unit transmitter-receiver, to the slave device, a wireless command signal containing a command instruction;
the slave device processor is configured to:
write the command stored instruction to the slave device memory to create a stored instruction, the slave device being configured to store only a single instruction in the slave device memory at any one time, wherein, after a first command instruction is stored and a second command instruction is received from the control master unit, the second command instruction over-writes the first command instruction;
read the stored instruction from the slave device memory; and
transmit via the slave device transmitter-receiver, to the control master unit, a wireless response signal containing the stored instruction;
the control master unit processor is further configured to:
compare the stored instruction to the command instruction; and, only if the stored instruction is the same as the command instruction, send a process instruction via the control master unit transmitter-receiver to the slave device.

2. The system according to claim 1, wherein the system is a medical system and the slave device is a delivery device for delivering therapy to a patient.

3. The system according to claim 2 wherein the medical system is a fluid delivery system, and the delivery device is a pumping device for pumping a therapeutic fluid.

4. The system according to claim 3, wherein the therapeutic fluid is insulin.

5. The system according to claim 1, wherein the slave device processor is configured to process the stored instruction only on receipt of the process instruction.

6. The system according to claim 1, wherein the slave device processor is configured to:
write the command instruction to a single, designated location in the slave device memory, and
read the stored instruction from the single, designated location in the memory.

7. The system according to claim 1, wherein the slave device and the control master unit communicate wirelessly using a radio frequency near field communication protocol.

8. The system according to claim 1, wherein the control master unit processor is further configured to, if the stored instruction is the same as the command instruction:
initiate a request for a user input; and,
in response to receiving an affirmative user input, send the process instruction via the control master unit transmitter-receiver to the slave device.

9. The system according to claim 1, wherein the control master unit processor is further configured to, if the stored instruction is the same as the command instruction:
automatically send the process instruction via the control master unit transmitter-receiver to the slave device.

10. The system according to claim 1, wherein, if the process instruction is not sent to the slave device, then the control master unit processor is configured to transmit again via the control master unit transmitter-receiver, to the slave device, the wireless command signal containing the command instruction.

11. The system according to claim 1, wherein, if the process instruction is sent to the slave device, then the slave device processor is further configured to:
transmit via the slave device transmitter-receiver, to the control master unit, a wireless signal containing information other than the command instruction.

12. A method of operating a system, the system comprising a slave device comprising a slave device memory and a control master unit for controlling the slave device, wherein the slave device and the control master unit are capable of communicating wirelessly with each other, the method comprising:

transmitting, from the control master unit to the slave device, a wireless command signal containing a command instruction;

at the slave device:
- writing the command instruction to the slave device memory to create a stored instruction, the slave device being configured to store only a single instruction in the slave device memory at any one time, wherein, after a first command instruction is stored and a second command instruction is received from the control master unit, the second command instruction over-writes the first command instruction;
- reading the stored instruction from the slave device memory; and
- transmitting, to the control master unit, a wireless response signal containing the stored instruction;

at the control master unit:
- comparing the stored instruction to the command instruction; and
- only if the stored instruction is the same as the command instruction, sending a process instruction to the slave device.

13. The method according to claim 12, wherein the system is a medical system and the slave device is a delivery device for delivering therapy to a patient.

14. The method according to claim 12, wherein processing the stored instruction comprises delivering therapy to a patient.

15. The method according to claim 13 wherein the medical system is a fluid delivery system, and the delivery device is a pumping device for pumping a therapeutic fluid.

16. The method according to claim 15, wherein the therapeutic fluid is insulin.

17. The method according to claim 12, further comprising, at the slave device:
- receiving the process instruction; and
- processing the stored instruction only once the process instruction has been received.

18. The method according to claim 12, wherein:
- the step of writing the command instruction to the slave device memory comprises writing the instruction to a single, designated location in the slave device memory; and
- the step of reading the stored instruction from the memory comprises reading a stored instruction from the single, designated location in the slave device memory.

19. The method according to claim 12, wherein the slave device and the control master unit communicate wirelessly using a radio frequency near field communication protocol.

20. The method according to claim 12 further comprising, at the control master unit, if the stored instruction is the same as the command instruction:
- requiring a user input; and,
- in response to receiving an affirmative user input, sending the process instruction to the slave device.

21. The method according to claim 12, further comprising, at the control master unit, if the stored instruction is the same as the command instruction:
- automatically sending the process instruction to the slave device.

* * * * *